(12) United States Patent
Majeed et al.

(10) Patent No.: US 10,555,982 B2
(45) Date of Patent: Feb. 11, 2020

(54) COMPOSITION CONTAINING OROXYLIN A AND METHOD OF EXTRACTION THEREOF

(71) Applicants: Muhammed Majeed, Edison, NJ (US); Kalyanam Nagabhushanam, East Windsor, NJ (US); Beena Bhat, Bangalore (IN); Anurag Pande, East Windsor, NJ (US)

(72) Inventors: Muhammed Majeed, Edison, NJ (US); Kalyanam Nagabhushanam, East Windsor, NJ (US); Beena Bhat, Bangalore (IN); Anurag Pande, East Windsor, NJ (US)

(73) Assignee: SAMI LABS LIMITED, Bangalore (IN)

( * ) Notice: Subject to any disclaimer, the term of this patent is extended or adjusted under 35 U.S.C. 154(b) by 0 days.

(21) Appl. No.: 15/805,320

(22) Filed: Nov. 7, 2017

(65) Prior Publication Data

US 2018/0344788 A1    Dec. 6, 2018

Related U.S. Application Data

(60) Provisional application No. 62/420,676, filed on Nov. 11, 2016.

(51) Int. Cl.
*A61K 31/352* (2006.01)
*A61K 36/185* (2006.01)
*A61K 31/7048* (2006.01)
*A61K 31/353* (2006.01)

(52) U.S. Cl.
CPC .......... *A61K 36/185* (2013.01); *A61K 31/352* (2013.01); *A61K 31/353* (2013.01); *A61K 31/7048* (2013.01); *A61K 2236/00* (2013.01); *A61K 2236/15* (2013.01); *A61K 2236/17* (2013.01); *A61K 2236/333* (2013.01); *A61K 2236/51* (2013.01)

(58) Field of Classification Search
CPC .................................................... A61K 31/352
See application file for complete search history.

(56) References Cited

U.S. PATENT DOCUMENTS

2007/0213281 A1* 9/2007 Rao ...................... A61K 31/353
514/27

OTHER PUBLICATIONS

English-language bibliographic information from Guo et al. (CN 1404831 A, 2003). (Year: 2003).*

* cited by examiner

*Primary Examiner* — Rosanne Kosson

(57) ABSTRACT

Disclosed are the compositions comprising bioactive components Oroxylin A, Baicalein, Chrysin, and their glucuronides Oroxylin A-7-glucuronide, Baicalein-7-glucuronide and Chrysin-7-glucuronide, isolated from the bark of *Oroxylum indicum*, and the process of isolating the said bioactives.

2 Claims, 20 Drawing Sheets

COMPOSITION CONTAINING OROXYLIN A AND METHOD OF EXTRACTION THEREOF

CROSS-REFERENCE TO RELATED PATENT APPLICATION

This is a non-provisional patent application claiming priority from U.S. Provisional Patent Application No. 62/420,676 filed on 11 Nov. 2016.

BACKGROUND OF THE INVENTION

Field of the Invention

The present invention in general relates to *Oroxylum indicum*. More specifically, the present invention relates to the isolation of bioactives Oroxylin A, Baicalein and Chrysin and their glucuronides from *Oroxylum indicum*.

Description of Prior Art

*Oroxylum indicum* (family: Bignoniaceae) or Broken bones tree, widely distributed throughout South East Asia, is an important herb in the ayurvedic system of medicine. The root and stem bark of this plant is reported to possess wide range of medicinal properties (Deka et al., *Oroxylum indicum*—a medicinal plant of North East India: An overview of its nutritional, remedial, and prophylactic properties, Journal of Applied Pharmaceutical Science, 2013, Vol. 3 (Suppl 1), S104-S112). Many important flavanoids isolated from the plant, namely Oroxylin A, Baicalein, Chrysin, Baicalin, Scutellarin, Hispidulin and their derivatives, attribute to its pharmacological property, many of which remain to be evaluated. Thus, there exists an unmet industrial need to isolate and identify the important actives present in *Oroxylum indicum* to validate their therapeutic potential.

Prior investigations have been able to successfully isolate the important bioactives present in the plant. Rao et al., U.S. Pat. No. 7,855,200, disclosed an hexane and acetone mediated process for the isolation of bioactives oroxylin A, Baicalein, Chrysin. But the processes are either expensive, time consuming or industrially non-viable. Hence, there exists a technical need for a novel process that is both economical and industrially viable. The present invention solves the said problem by disclosing a novel process for the isolation of bioactives from *Oroxylum indicum*.

It is the principle objective of the present invention to disclose a non-obvious and industrially applicable process for the isolation of bioactives Oroxylin A, Baicalein, Chrysin, and their glucuronides from *Oroxylum indicum*.

It is another objective of the present invention to disclose a novel composition comprising oroxylin A, Baicalein, Chrysin and their glucuronides.

The present invention fulfils aforesaid objectives and provides further related advantages.

SUMMARY OF THE INVENTION

The invention discloses a process for the isolation of bioactive components Oroxylin A, Baicalein, Chrysin, and their glucuronides Oroxylin A-7-glucuronide, Baicalein7-glucuronide and Chrysin7-glucuronide from the bark of *Oroxylum indicum*. The invention also discloses compositions comprising said bioactive components Oroxylin A, Baicalein, Chrysin, and their glucuronide components Oroxylin A-7-glucuronide, Baicalein-7-glucuronide and Chrysin-7-glucuronide.

DESCRIPTION OF THE MOST PREFERRED EMBODIMENTS

The present invention discloses a process for extraction of a composition containing Oroxylin A and its glucuronides from *Oroxylum indicum*, said process comprising steps of:

a) Cutting, drying and pulverising the bark of *Oroxylum indicum* into fine powder
b) Extracting 100 kg of the fine powder of step a) with 80% methanol (v/v) to obtain an aqueous methanol extract.
c) Dissolving the aqueous methanol extract of step b) in water to yield a turbid solution
d) Extracting the turbid solution of step c) using an organic solvent
e) Concentrating and drying the solvent fraction of step d) to obtain a yellow brown colour powder
f) Characterising bioactives present in the powder of step d) using HPLC, NMR and Mass spectrometry as Oroxylin A, as represented by STR #1, Baicalein, as represented by STR #2 and Chrysin, as represented by STR #3

STR#1
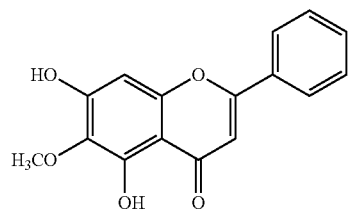

STR#2
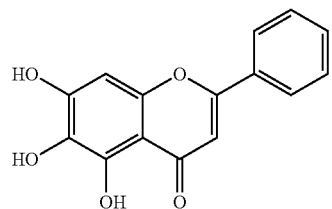

STR#3
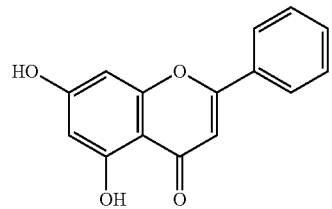

g) Concentrating and drying the aqueous fraction of step d) to obtain a brown colour powder
h) Characterising bioactives present in the powder of step g) using HPLC, NMR and Mass spectrometry as Oroxylin A-7-glucuronide, as represented by STR #4, Baicalein-7-glucuronide, as represented by STR #5 and Chrysin-7-glucuronide, as represented by STR #6

STR#4
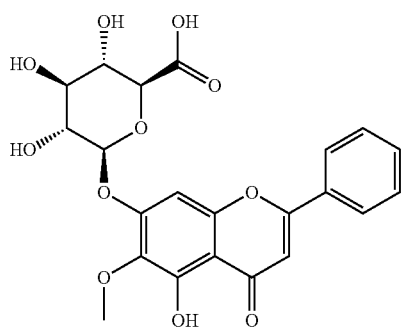

STR#5
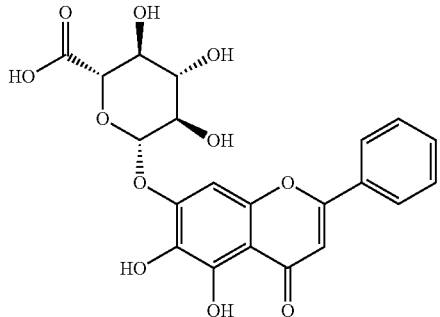

STR#6

In a related embodiment, the organic solvent of step d) is selected from the group consisting of hexane, ethyl acetate, methanol, ethanol, chloroform, butanol and acetone. In another related embodiment, the organic solvent of step d) is preferably ethyl acetate.

In another embodiment, the present invention discloses a composition comprising of not less than 10% of Oroxylin A, not less than 10% of Baicalein and not less than 2% of Chrysin, isolated from the bark of *Oroxylum indicum*. In further specific embodiments, the present invention discloses a composition comprising from about 10%-15% of Oroxylin A, about 10%-25% of Baicalein and about 2%-10% of Chrysin, isolated from the bark of *Oroxylum indicum*.

In another related embodiment, the present invention discloses a composition comprising not less than 0.5% of Oroxylin A-7-glucuronide, not less than 2% of Baicalein-7-glucuronide and not less than 0.5% of Chrysin-7-glucuronide, isolated from the bark of *Oroxylum indicum*. In further specific embodiments, the present invention discloses a composition comprising from about 0.5%-8% of Oroxylin A-7-glucuronide, from about 2%-10% of Baicalein-7-glucuronide and about 0.5%-5% of Chrysin-7-glucuronide, isolated from the bark of *Oroxylum indicum*.

The aforesaid most preferred embodiments incorporating the technical features and technical effects of instant invention, are explained through illustrative examples herein under.

Example 1: Isolation and Identification of Bioactives from *Oroxylum indicum*

Figure 1:
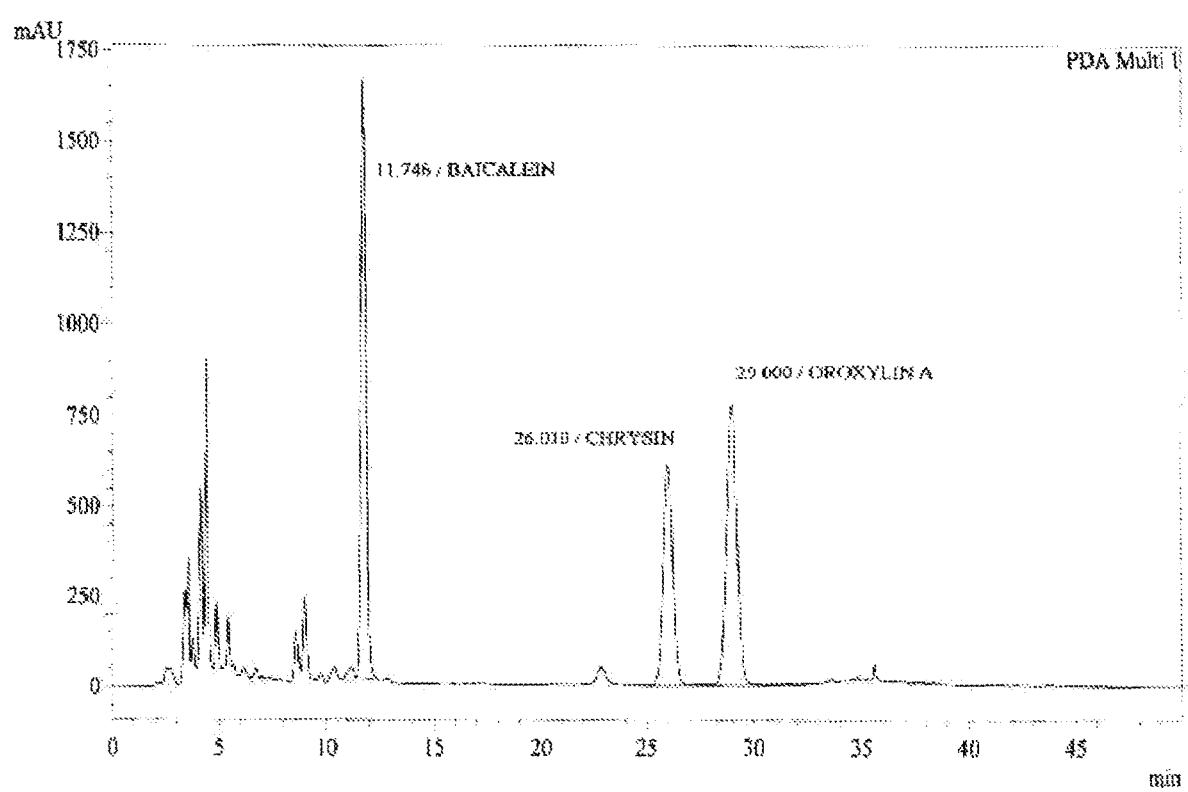
FIG. 1 shows the HPLC chromatogram for the identification of Oroxylin A. Baicalein, and Chrysin isolated from of the bark of *Oroxylum indicum*.
Figure 2:
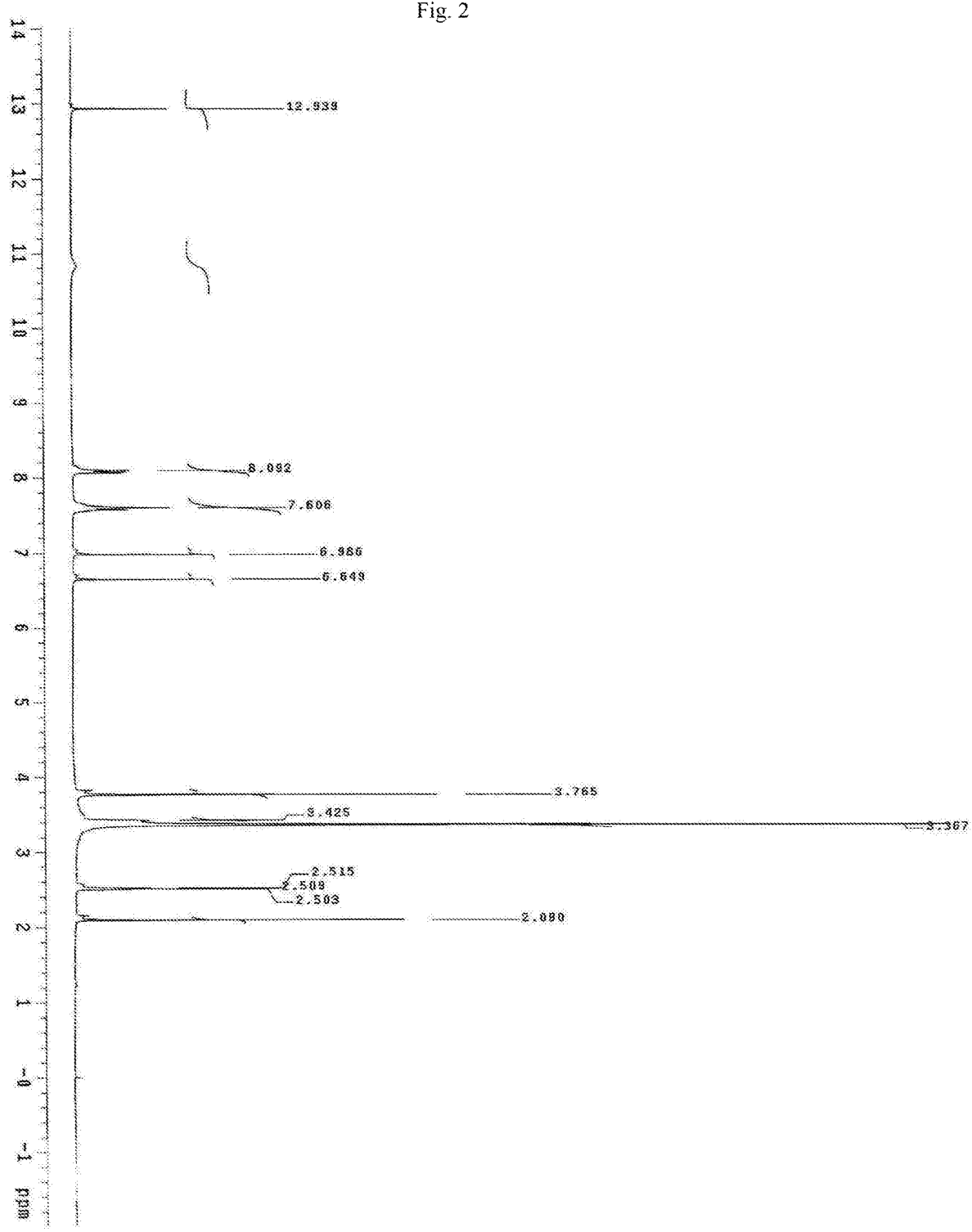
FIG. 2 shows the proton NMR spectrum for the identification of Oroxylin A isolated from of the bark of *Oroxylum indicum*.
Figure 3:
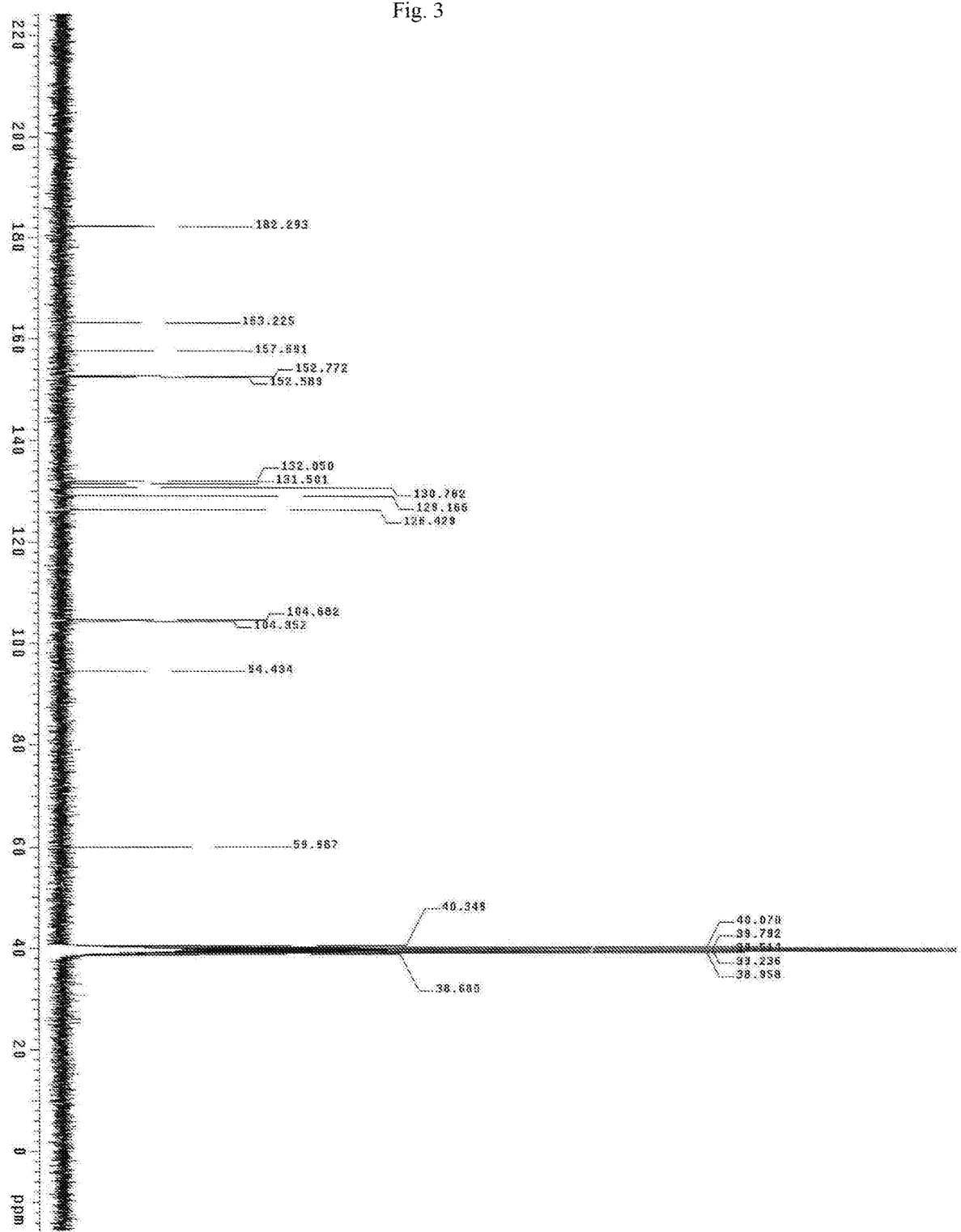
FIG. 3 shows the Carbon NMR spectrum for the identification of Oroxylin A isolated from of the bark of *Oroxylum indicum*.
Figure 4:
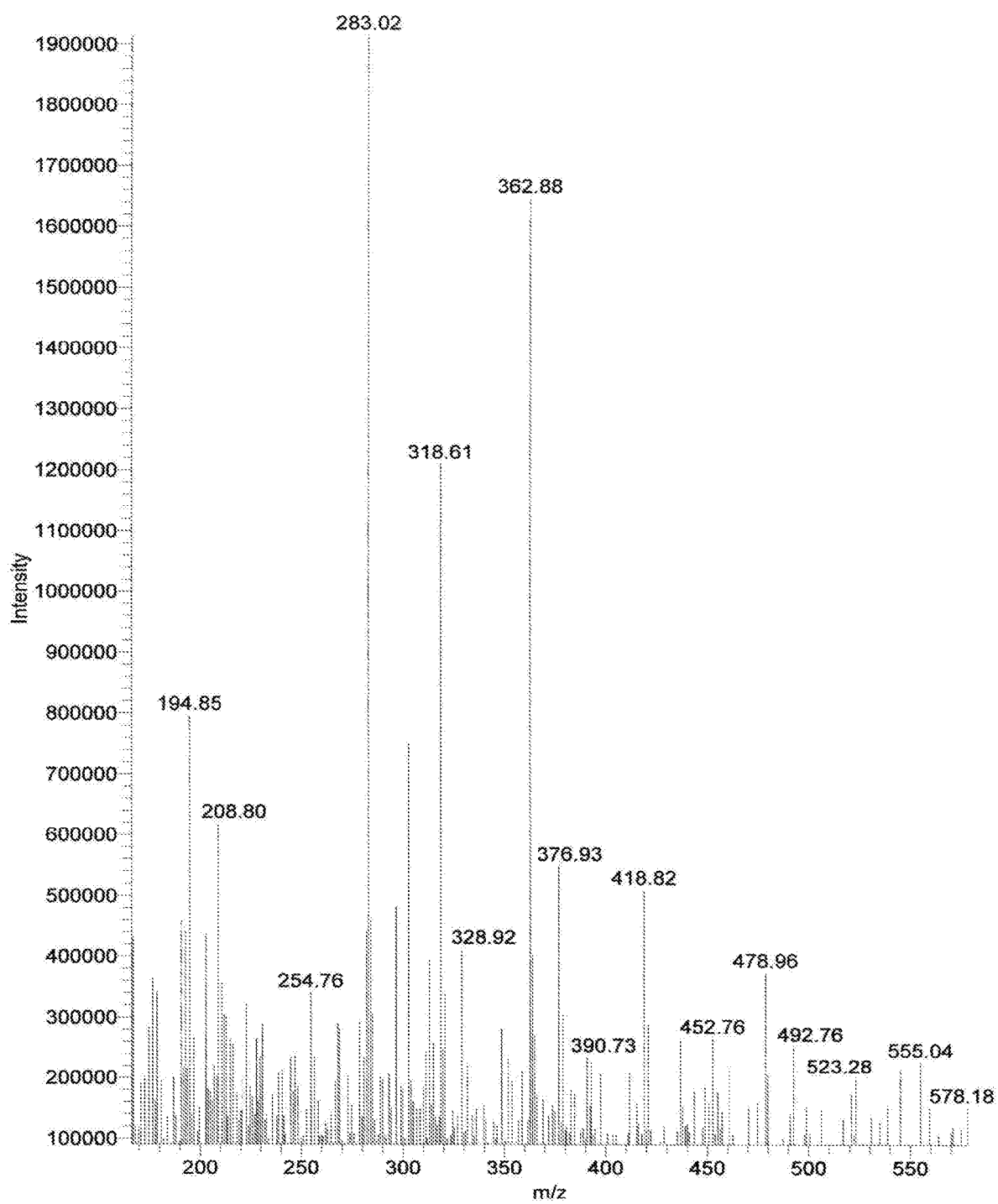
FIG. 4 shows the mass spectrometric data of Oroxylin A isolated from of the bark of *Oroxylum indicum*.
Figure 5:
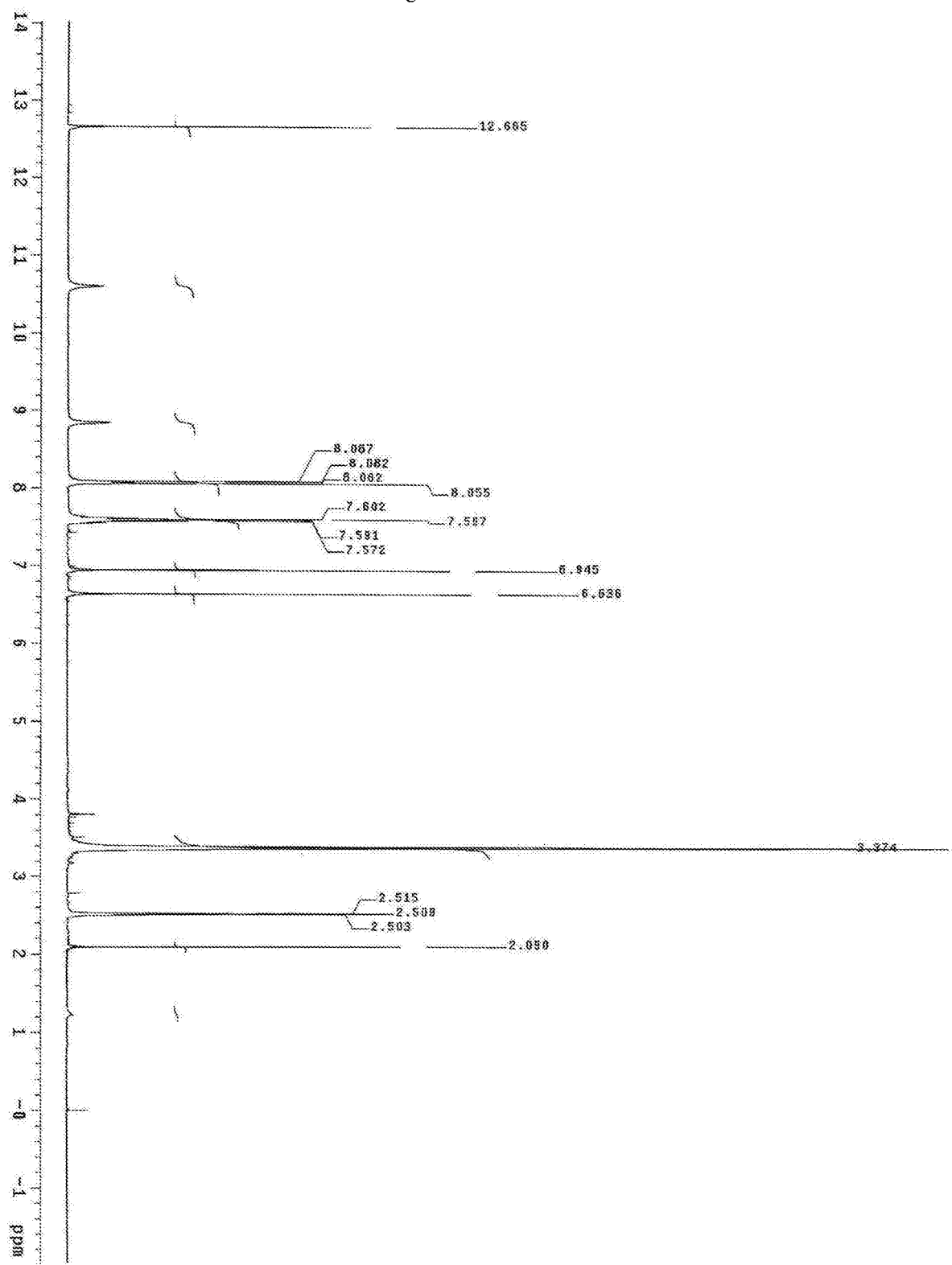
FIG. 5 shows the proton NMR spectrum for the identification of Baicalein isolated from of the bark of *Oroxylum indicum*.
Figure 6:
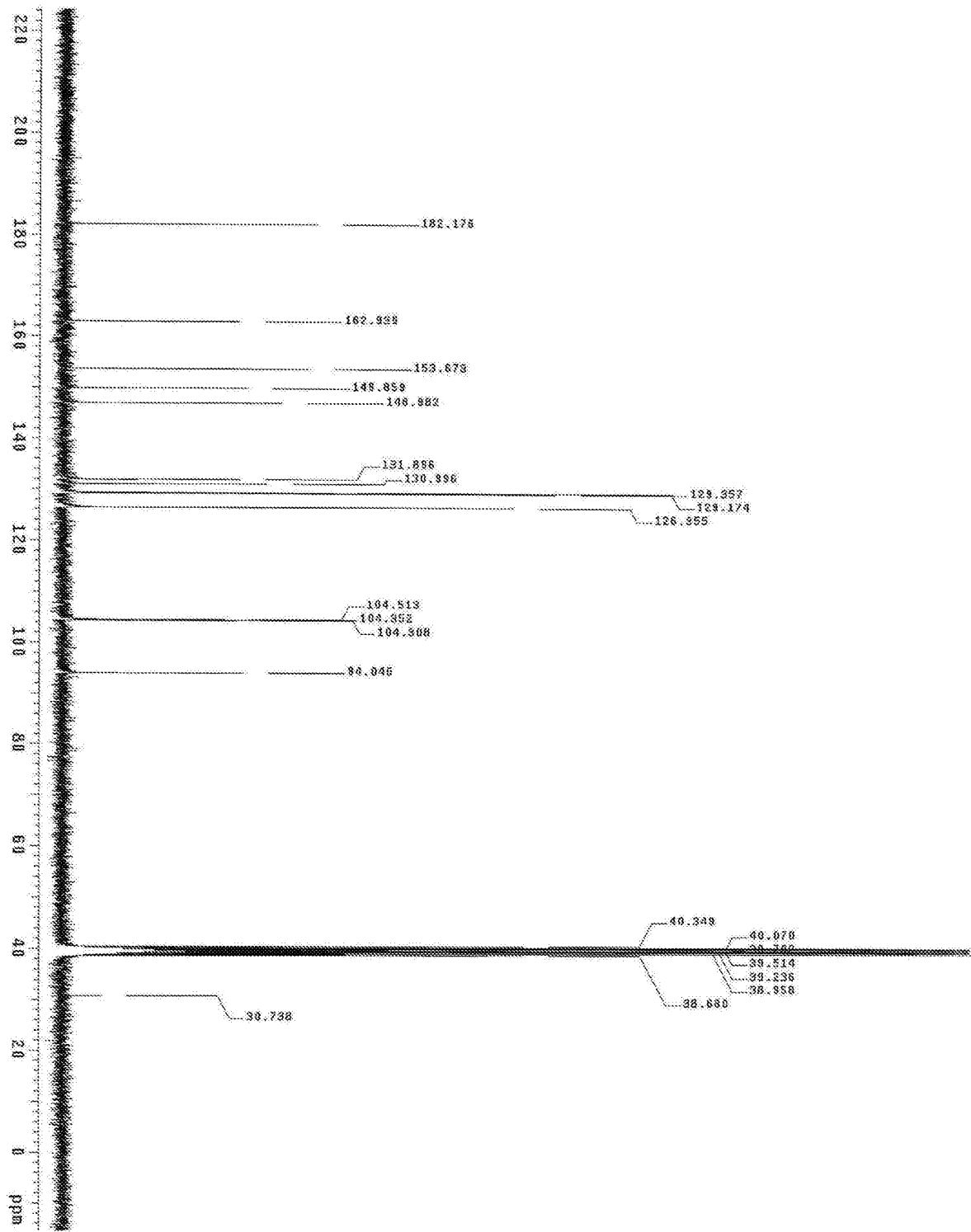
FIG. 6 shows the Carbon NMR spectrum for the identification of Baicalein isolated from of the bark of *Oroxylum indicum*.
Figure 7:
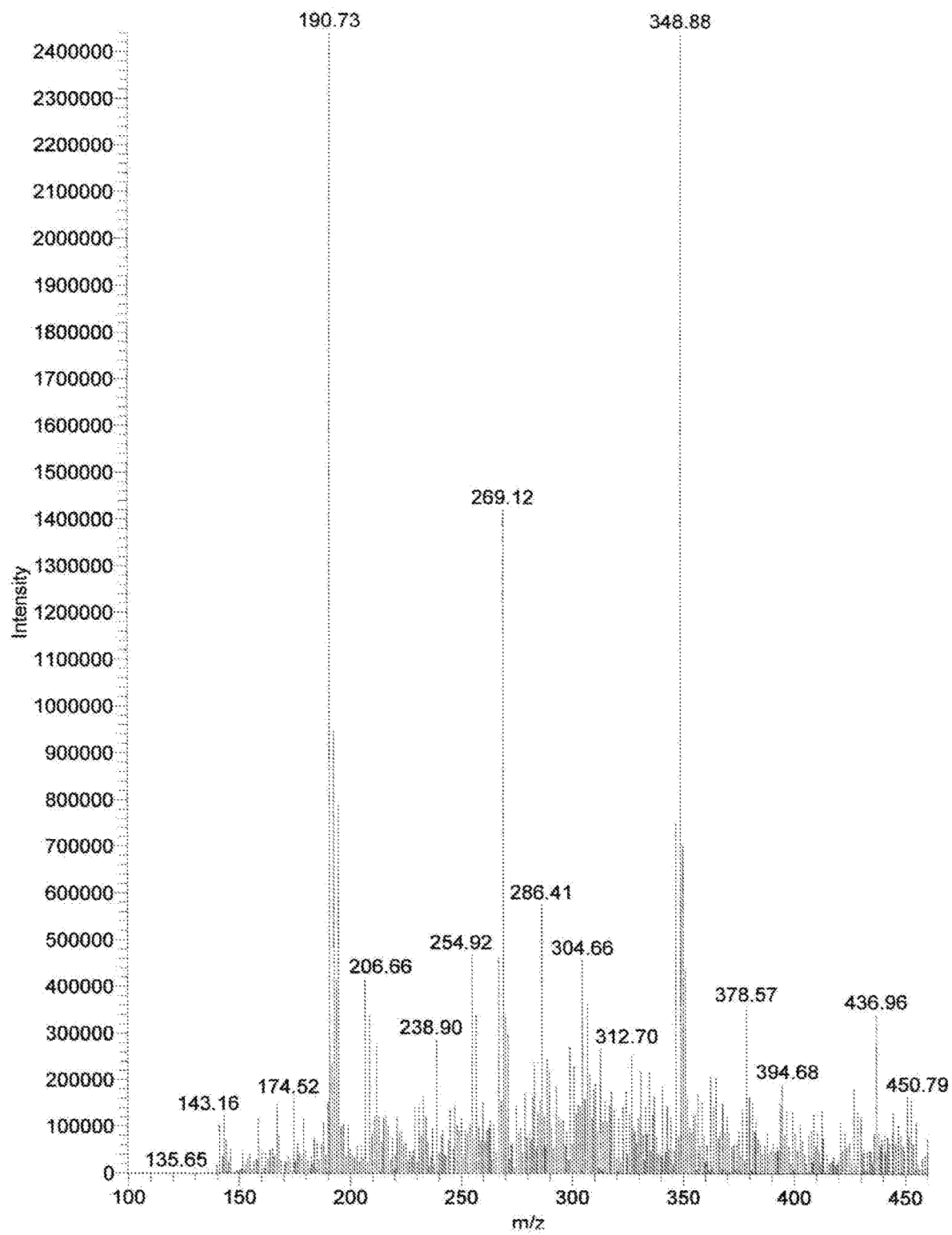
FIG. 7 shows the mass spectrometric data of Baicalein isolated from of the bark of *Oroxylum indicum*.
Figure 8:
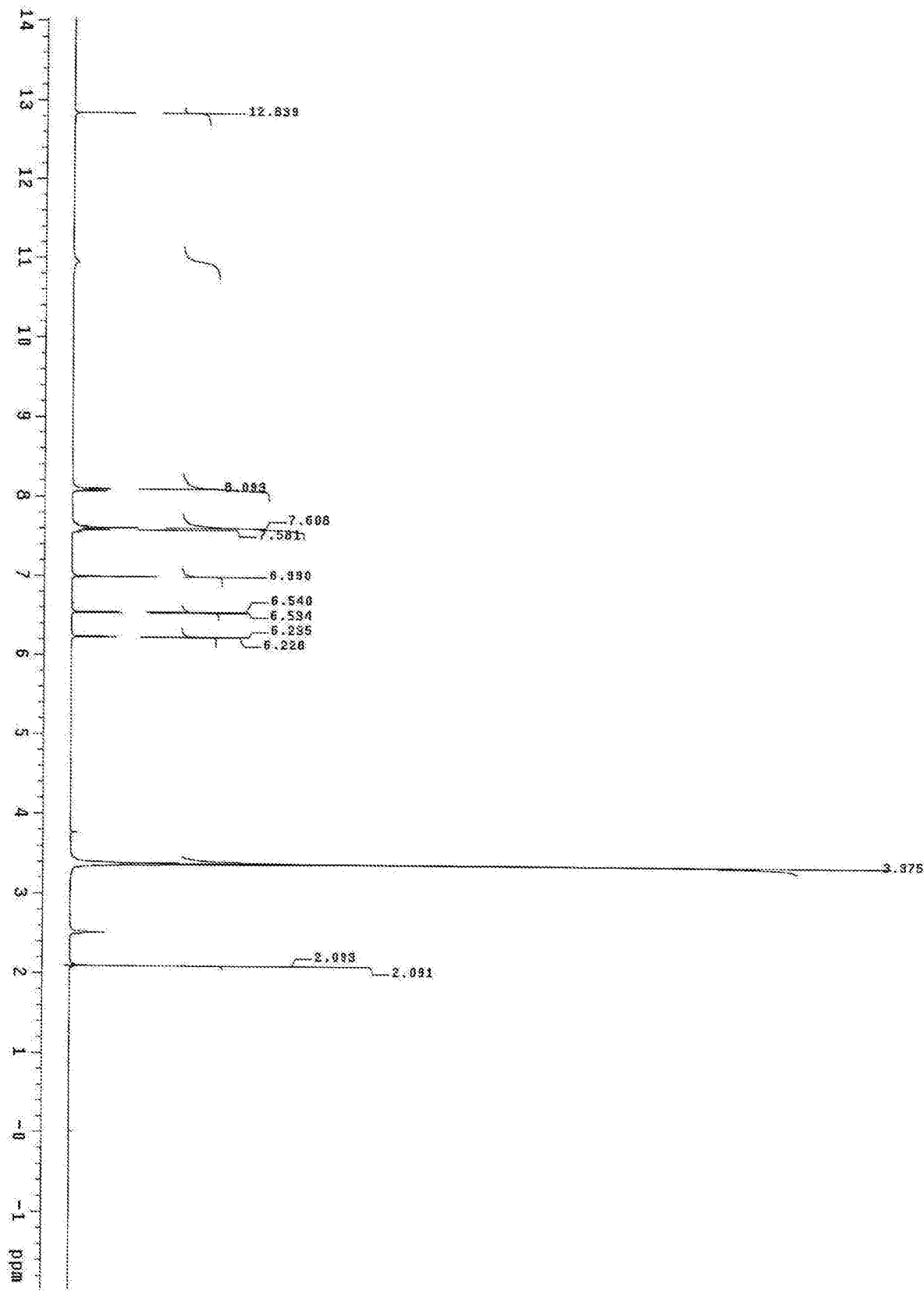
FIG. 8 shows the proton NMR spectrum for the identification of Chrysin isolated from of the bark of *Oroxylum indicum*.
Figure 9:
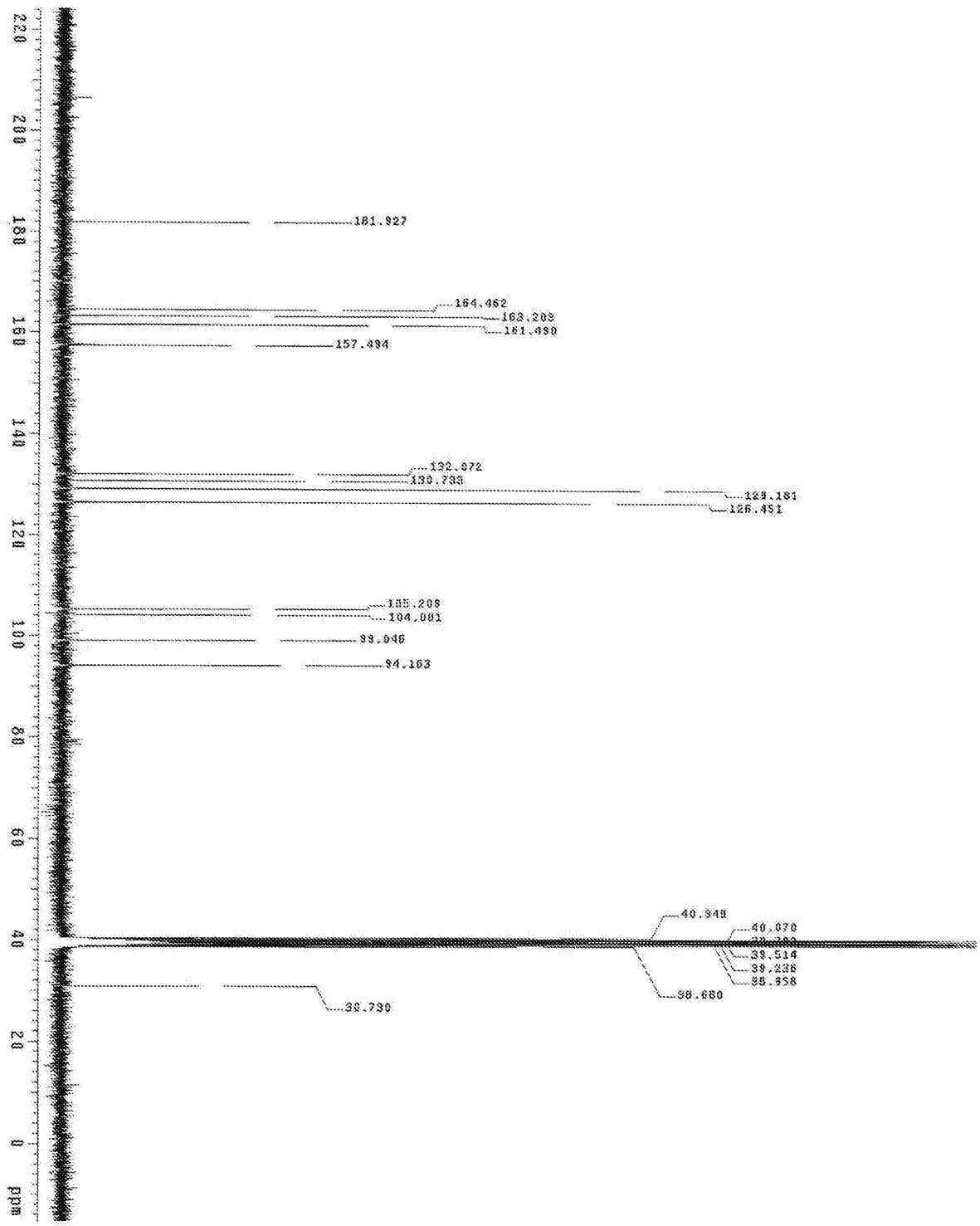
FIG. 9 shows the carbon NMR spectrum for the identification of Chrysin isolated from of the bark of *Oroxylum indicum*.
Figure 10:
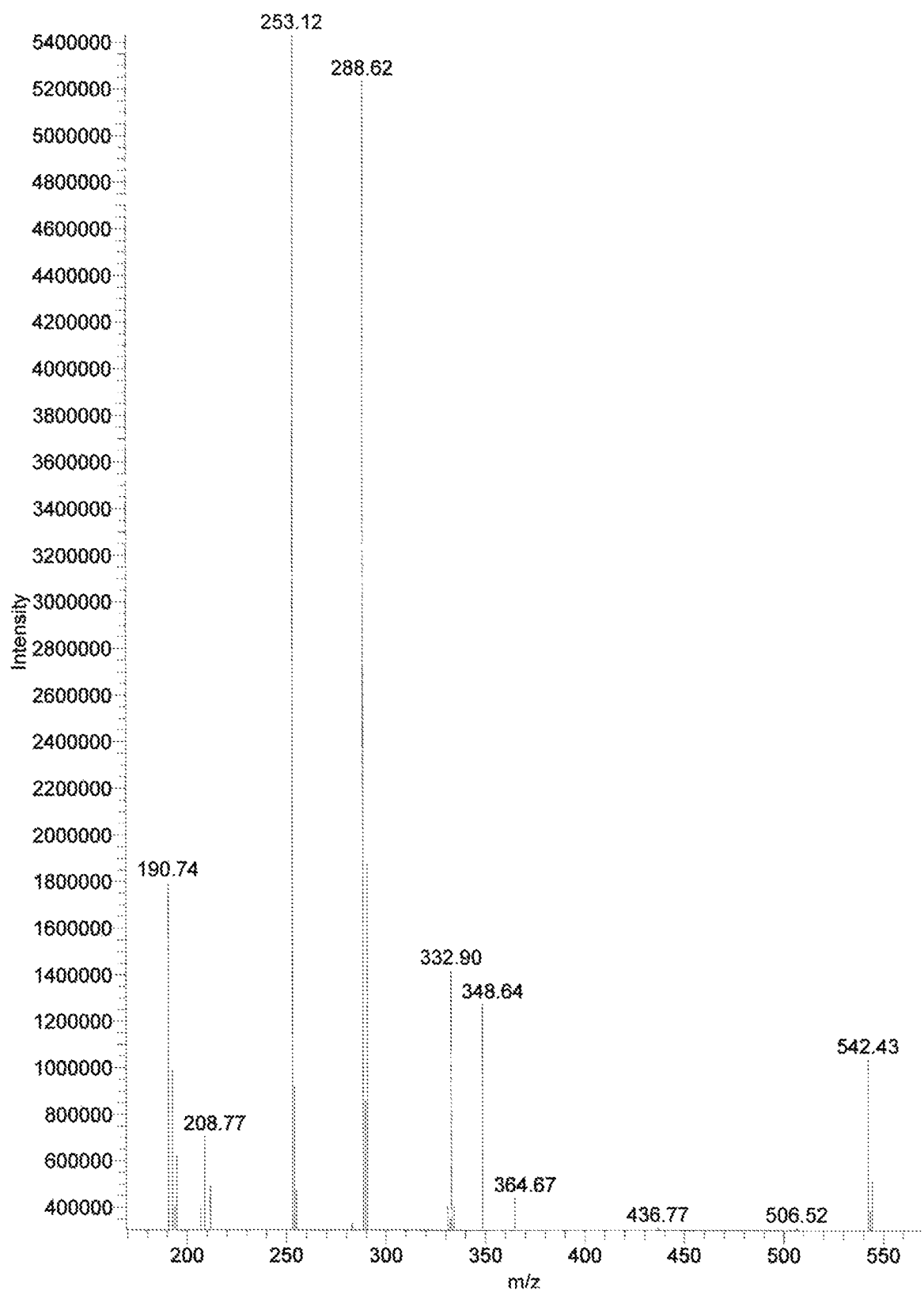
FIG. 10 shows the mass spectrometric data of Chrysin isolated from of the bark of *Oroxylum indicum*.

*Oroxylum indicum* is widely distributed throughout South East Asia. For isolating and identifying the bioactives present in the plant, the bark was cut, dried and pulverised into a fine powder. 100 kg of the fine powder of was extracted with 80% methanol (v/v) to obtain an aqueous methanol extract. This was further dissolved in water to obtain a turbid solution. The turbid solution was further extracted with ethyl acetate. The ethyl acetate fraction was separated, concentrated and dried to obtain a yellow brown colour powder. The bioactives present in the yellow powder was separated and identified using HPLC (FIG. 1) and further characterised using NMR and mass spectrometer as Oroxylin A (FIGS. 2-4), Baicalein (FIGS. 5-7) and Chrysin (FIGS. 8-10) as represented by STR #1, STR #2 and STR #3 respectively.

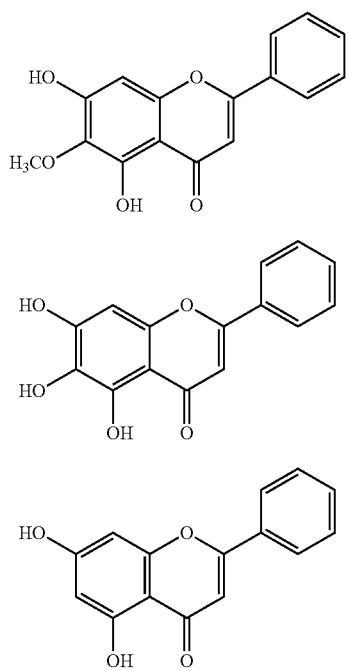

STR#1

STR#2

STR#3

Figure 11:
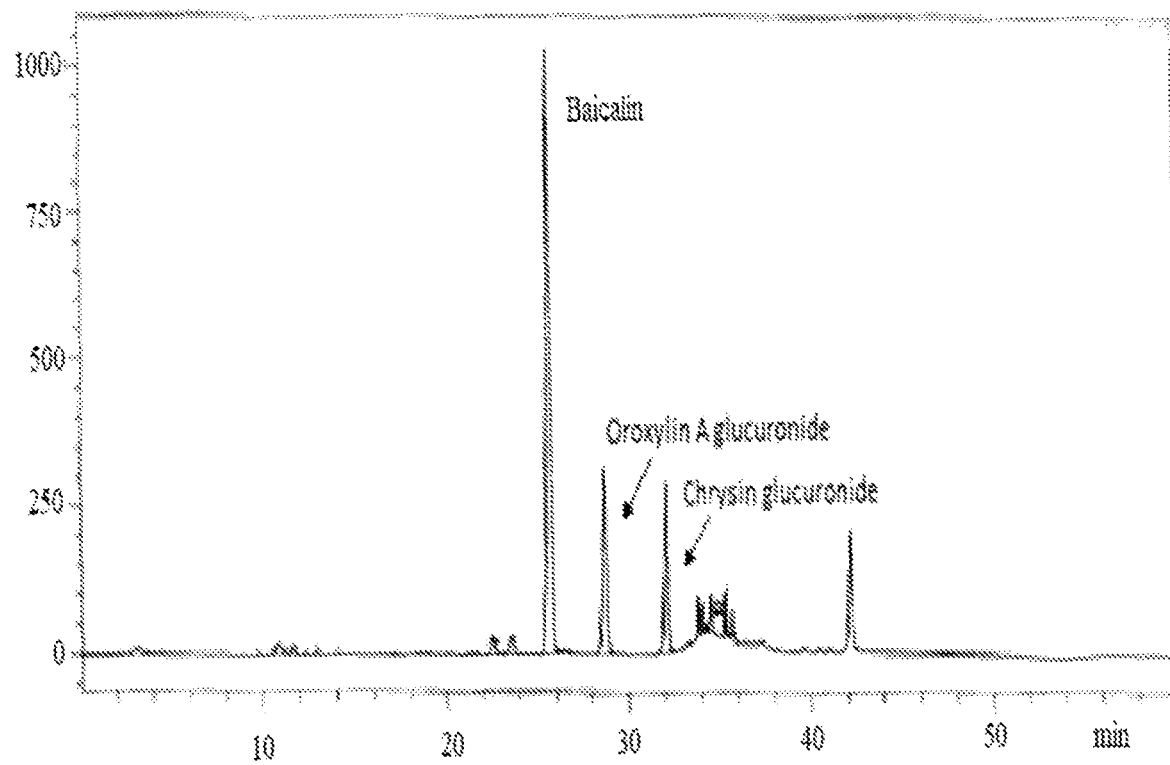
FIG. 11 shows the HPLC chromatogram for the identification of Oroxylin A-7-glucuronide, Baicalein-7-glucuronide, and Chrysin-7-glucuronide isolated from of the bark of *Oroxylum indicum*.
Figure 12:
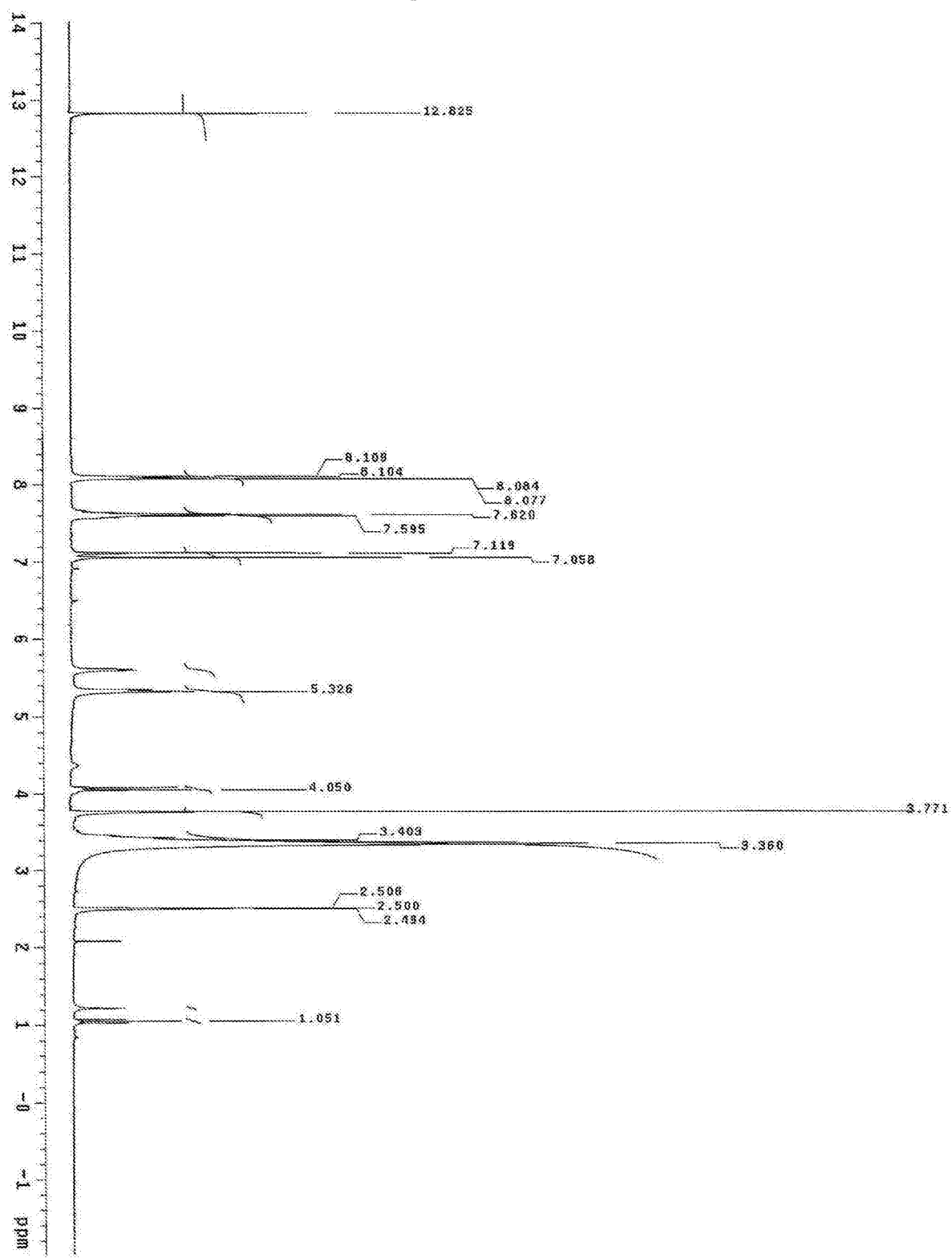
FIG. 12 shows the proton NMR spectrum for the identification of Oroxylin A-7-glucuronide isolated from of the bark of *Oroxylum indicum*.
Figure 13:
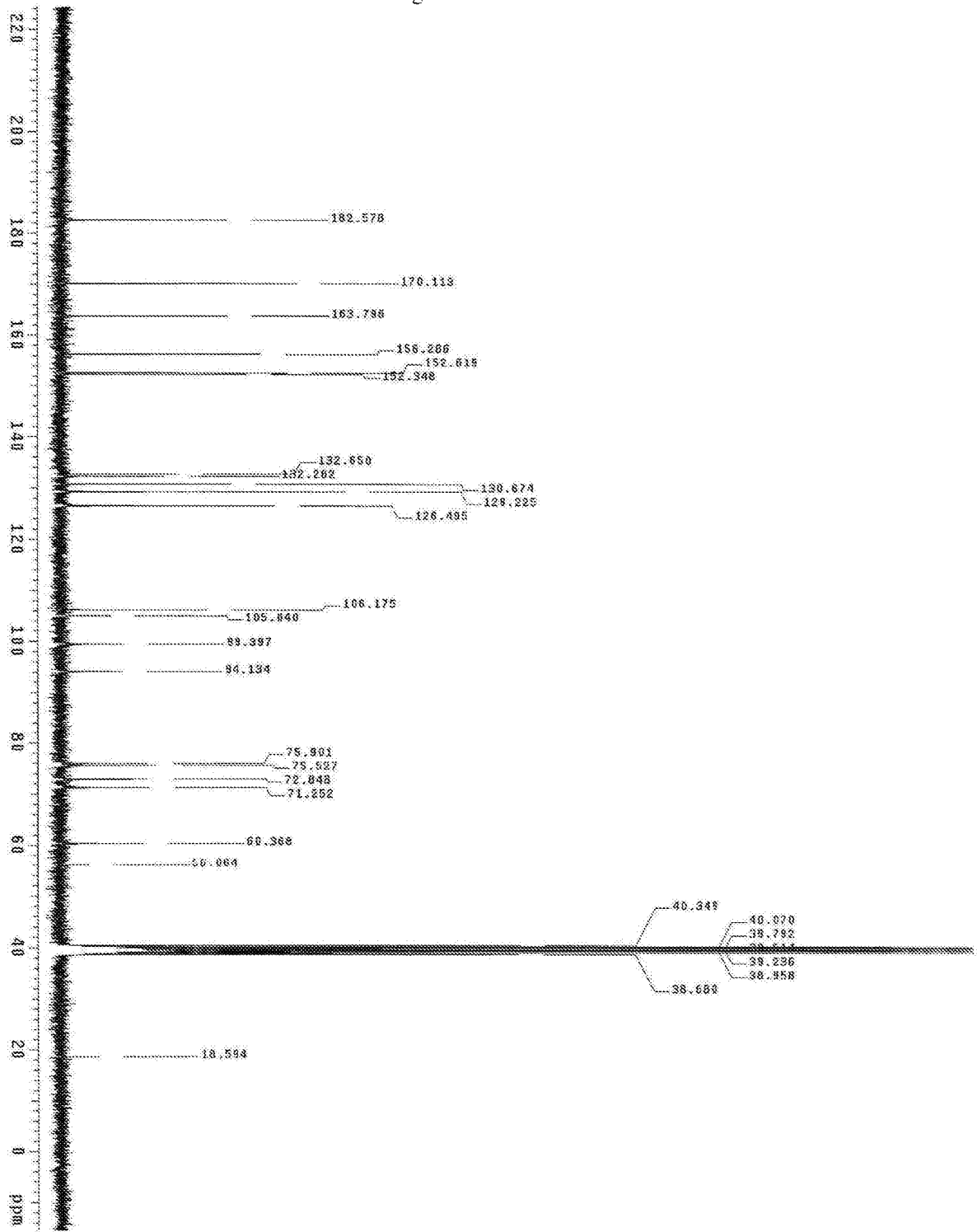
FIG. 13 shows the Carbon NMR spectrum for the identification of Oroxylin A-7-glucuronide isolated from of the bark of *Oroxylum indicum*.
Figure 14:
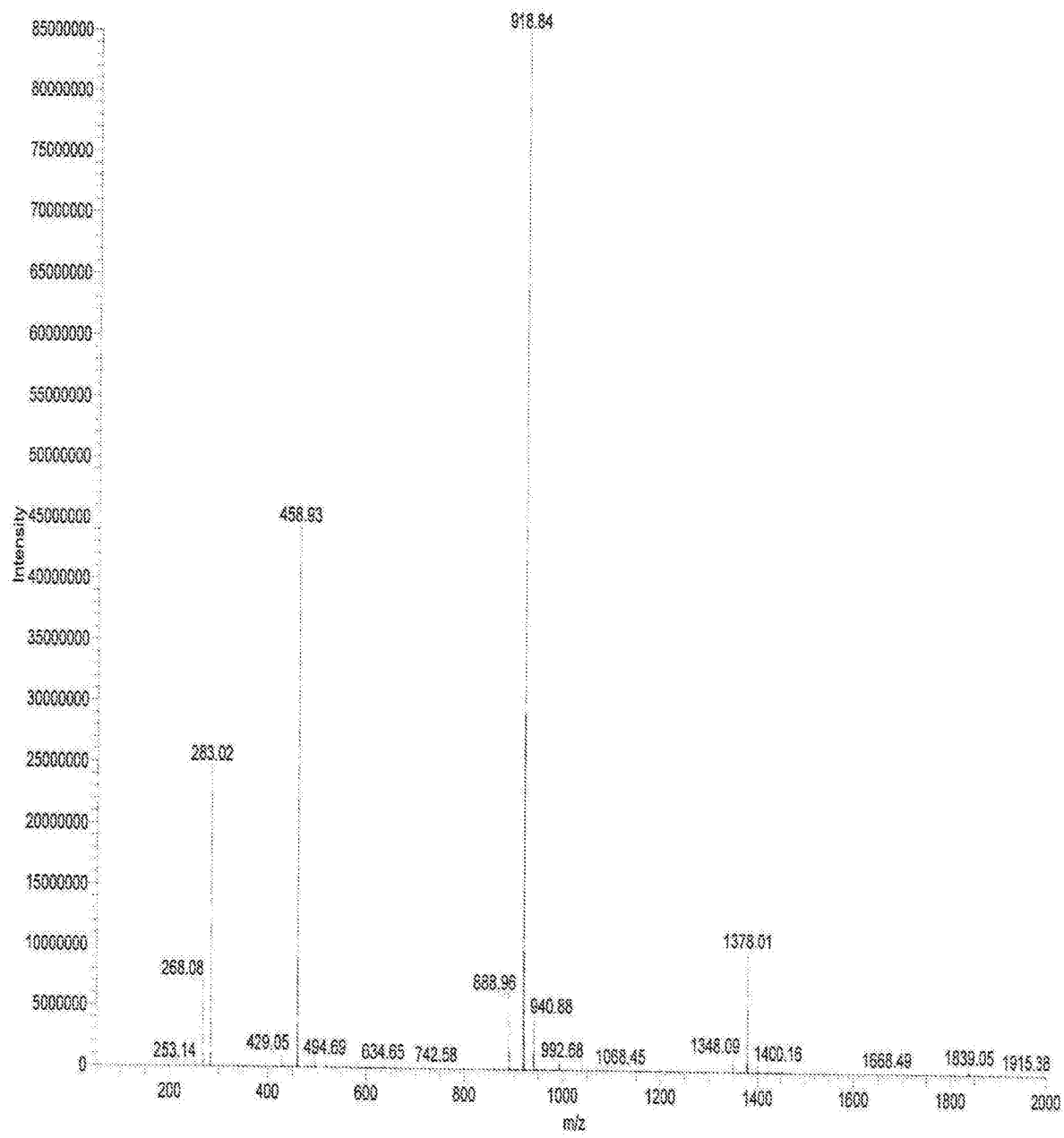
FIG. 14 shows the mass spectrometric data of Baicalein-7-glucuronide isolated from of the bark of *Oroxylum indicum*.
Figure 15:
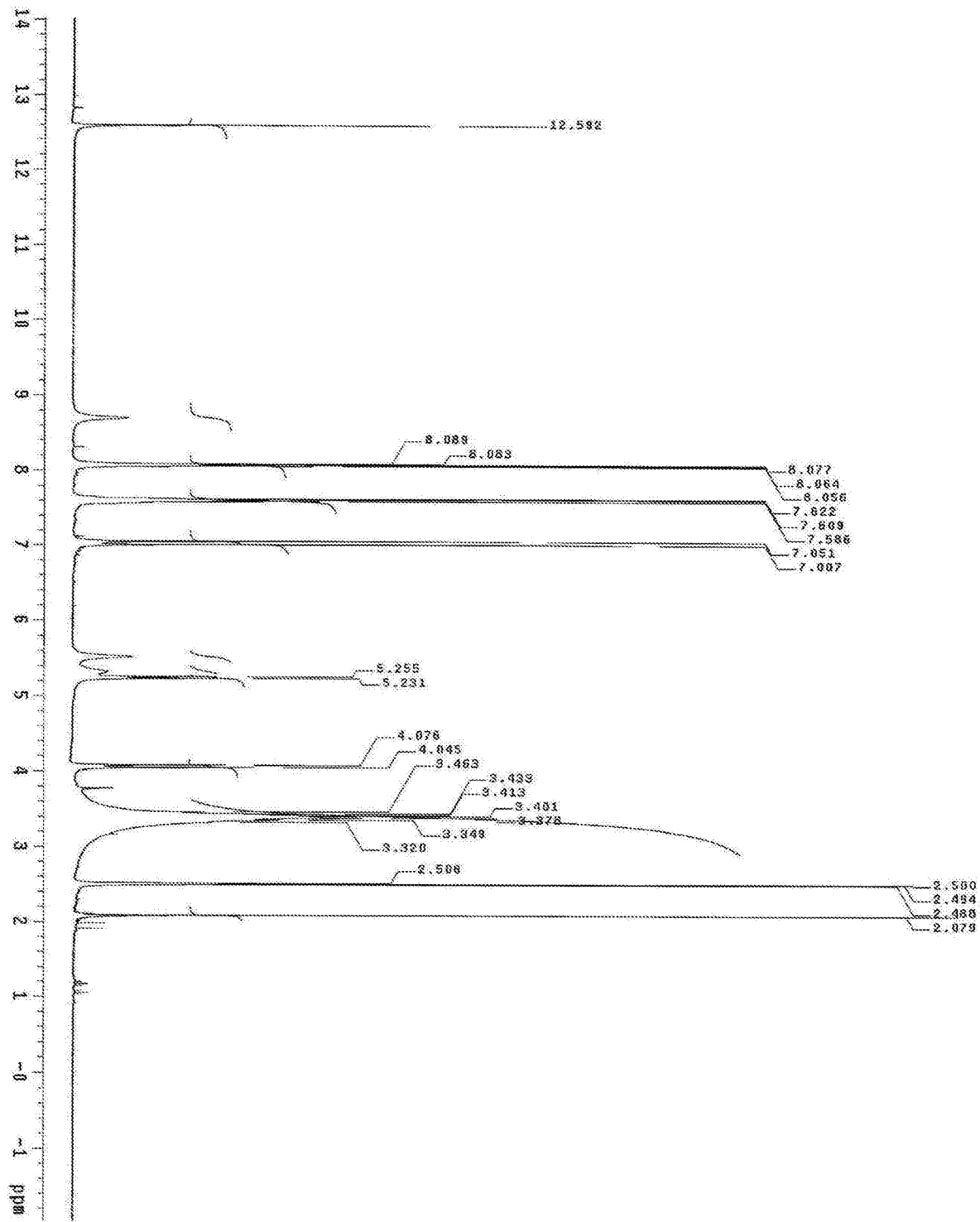
FIG. 15 shows the proton NMR spectrum for the identification of Baicalein-7-glucuronide isolated from of the bark of *Oroxylum indicum*.
Figure 16:
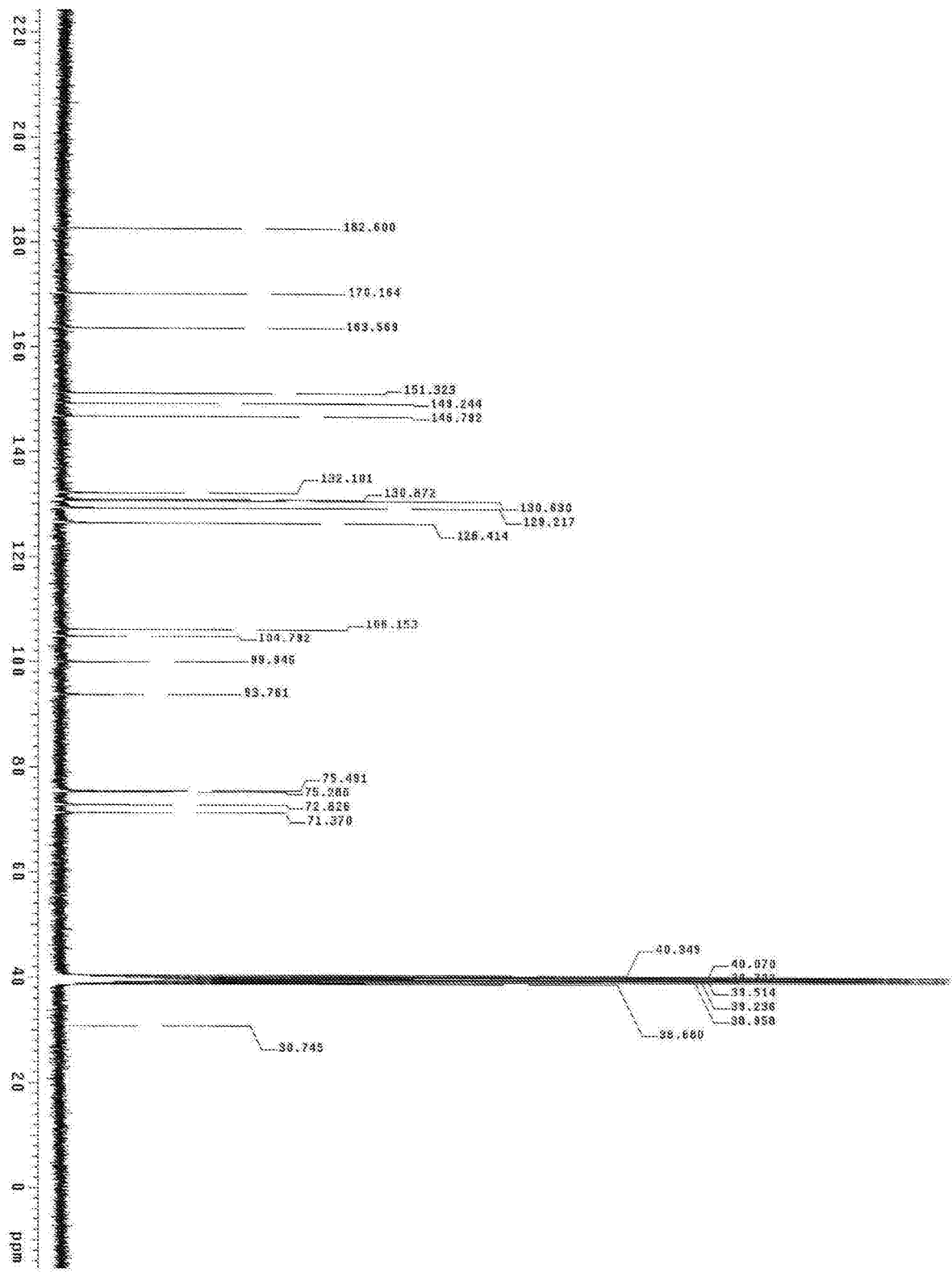
FIG. 16 shows the Carbon NMR spectrum for the identification of Baicalein-7-glucuronide isolated from of the bark of *Oroxylum indicum*.
Figure 17:
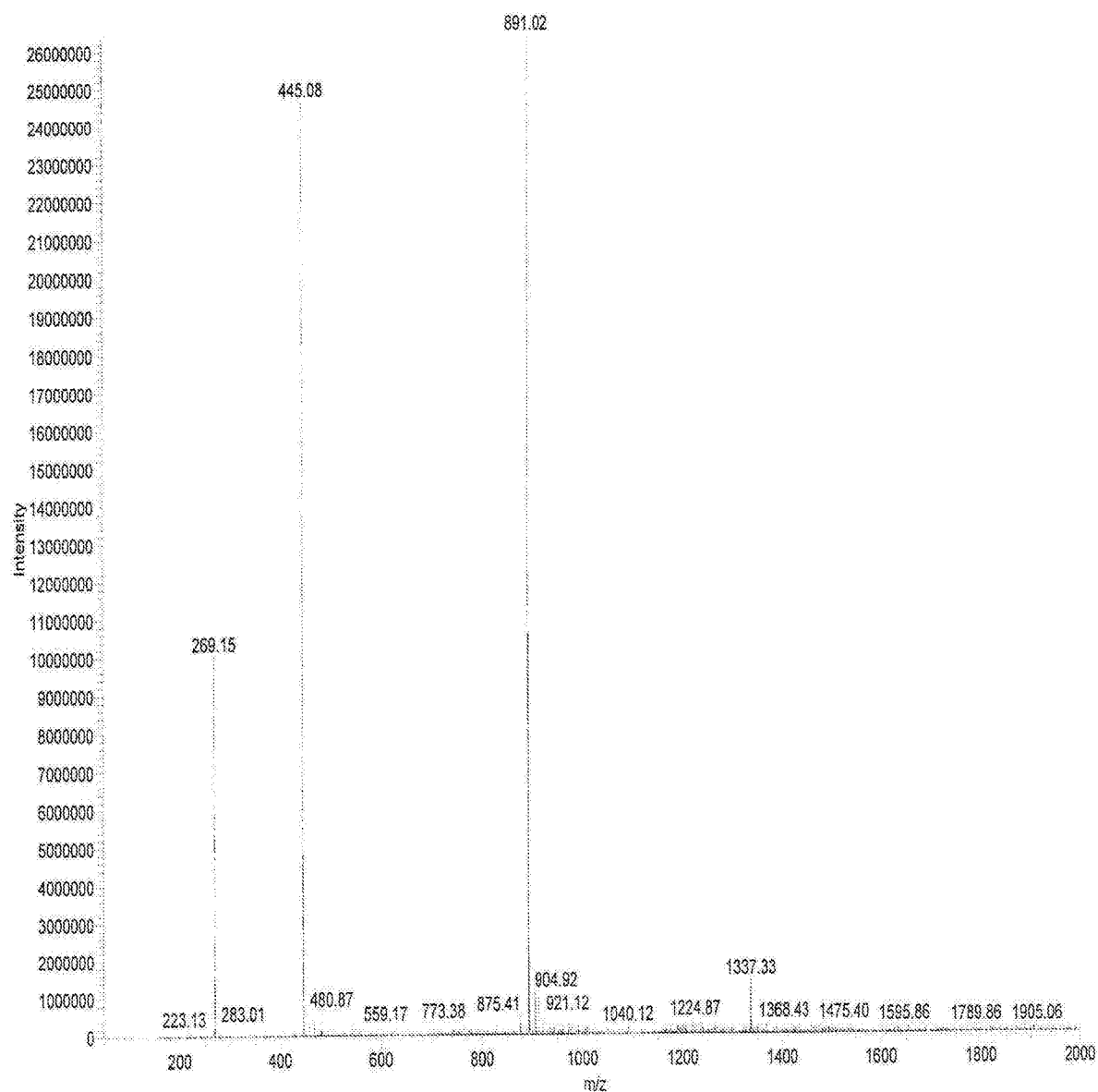
FIG. 17 shows the mass spectrometric data of Baicalein-7-glucuronide isolated from of the bark of *Oroxylum indicum*.
Figure 18:
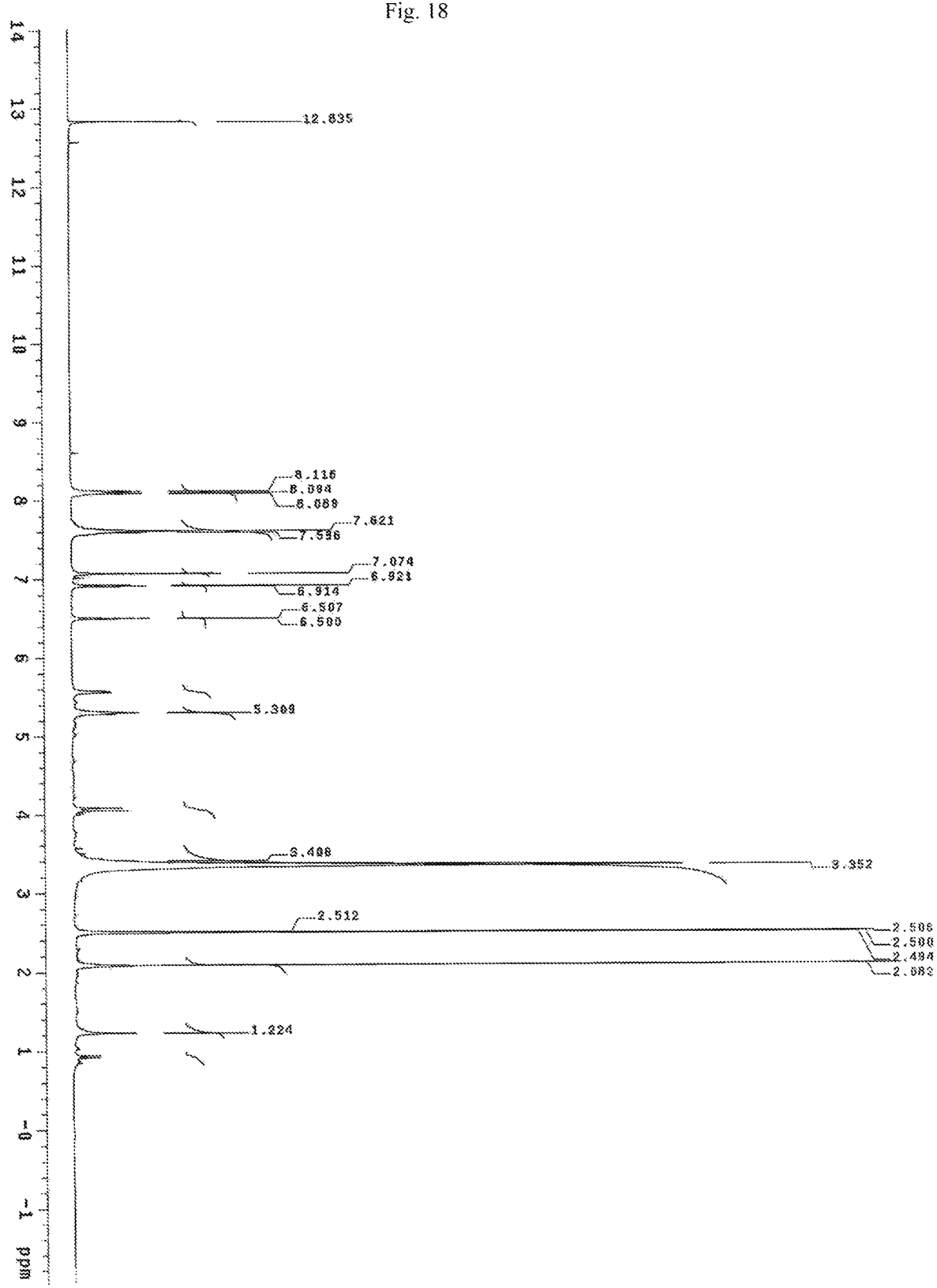
FIG. 18 shows the proton NMR spectrum for the identification of Chrysin-7-glucuronide isolated from of the bark of *Oroxylum indicum*.
Figure 19:
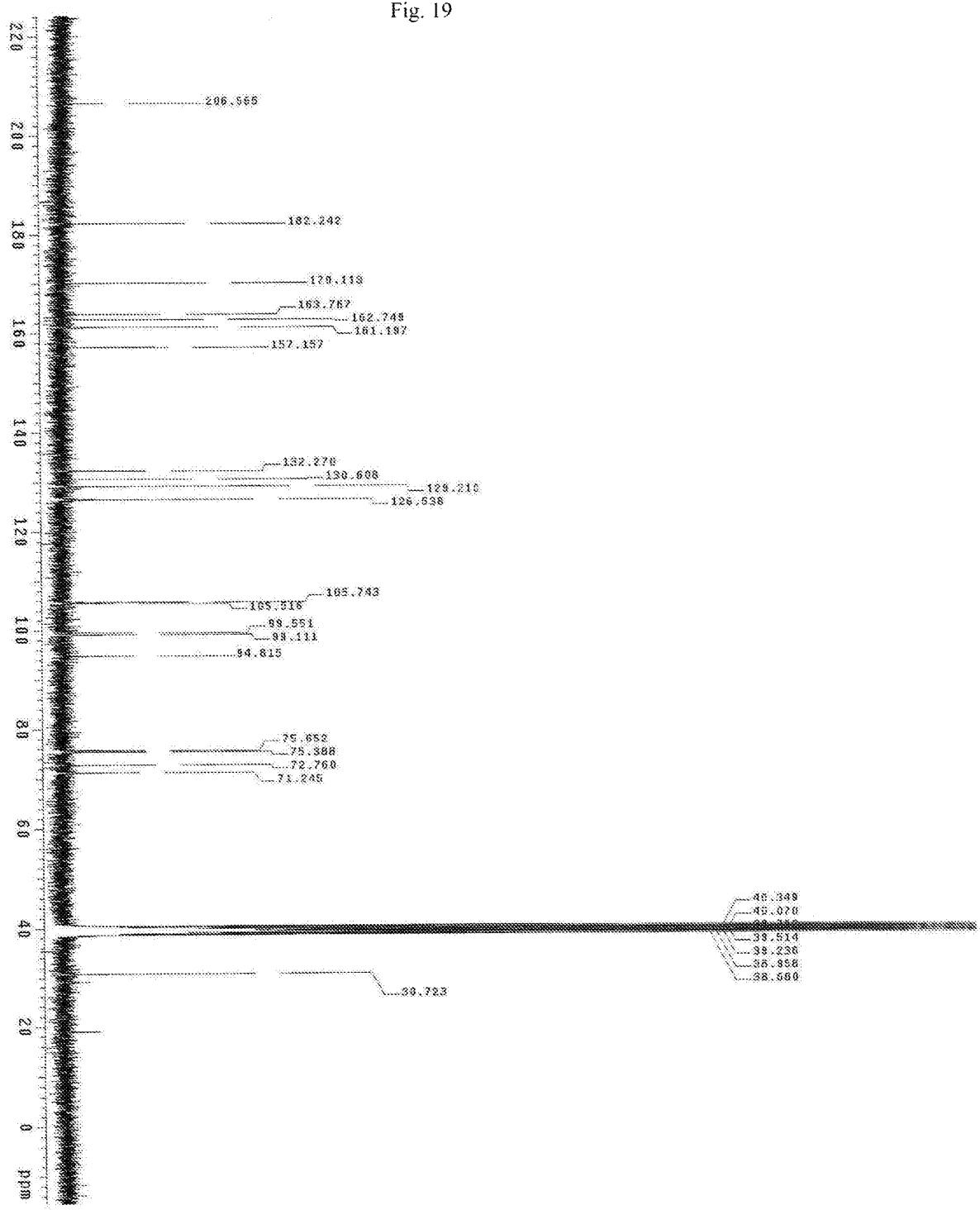
FIG. 19 shows the Carbon NMR spectrum for the identification of Chrysin-7-glucuronide isolated from of the bark of *Oroxylum indicum*.
Figure 20:
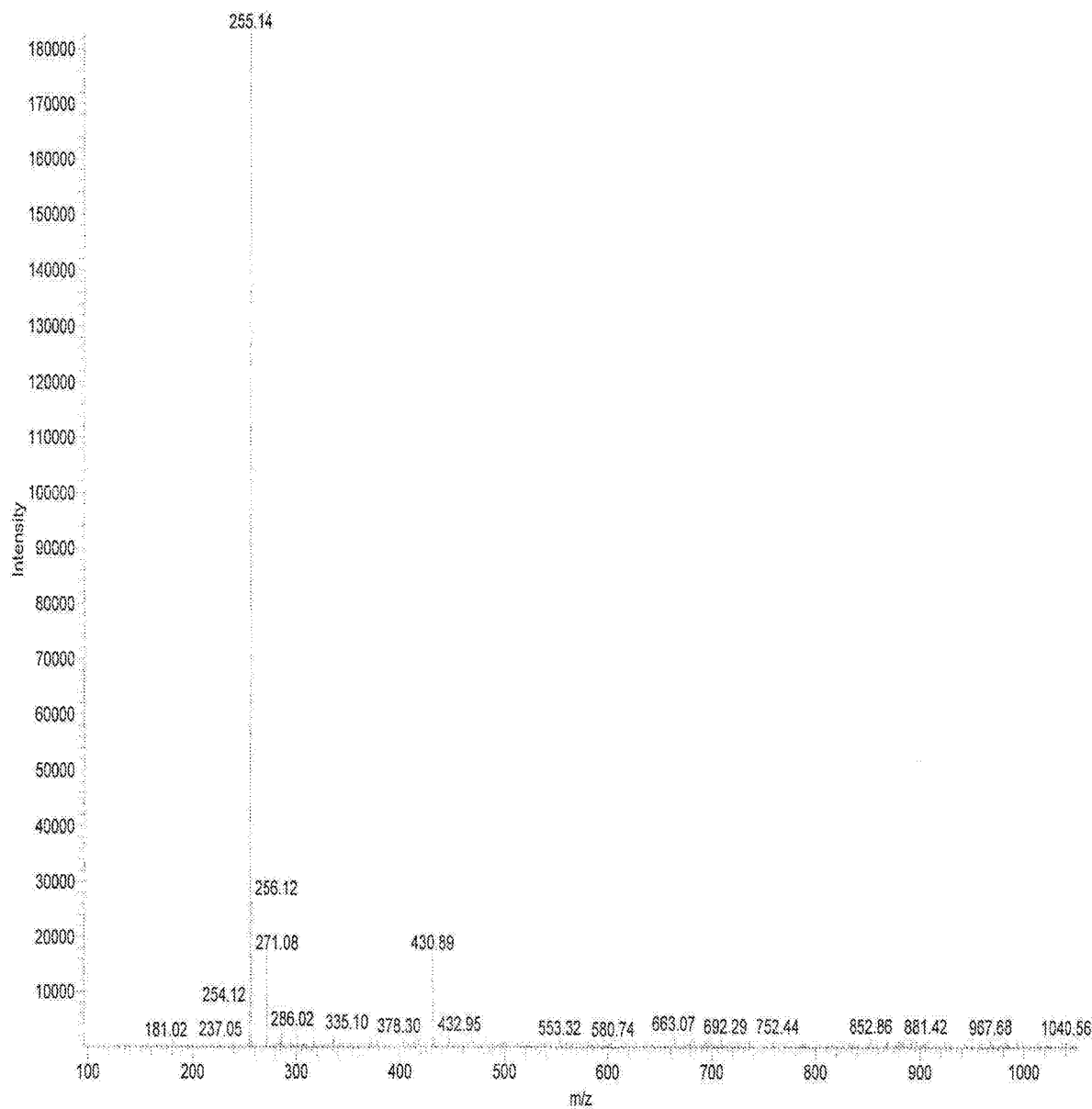
FIG. 20 shows the mass spectrometric data of Chrysin-7-glucuronide isolated from of the bark of *Oroxylum indicum*.

The aqueous fraction was further concentrated and dried to obtain a brown colour powder. The bioactives present in the brown powder (aq. Fraction) was separated and identified using HPLC (FIG. 11) and further characterised using NMR and mass spectrometer as Oroxylin A-7-glucuronide (FIGS. 12-14), Baicalein-7-glucuronide (FIGS. 15-17) and Chrysin-7-glucuronide (FIGS. 18-20), as represented by STR #4, STR #5 and STR #6 respectively.

The content of the bioactives, isolated from the bark of *Oroxylum indicum*, is tabulated in table 1.

TABLE 1

Content of identified molecules in ethyl acetate fraction and water soluble fraction

| Ethyl acetate fraction | | Aqueous fraction | |
|---|---|---|---|
| Bioactive | Concentration | Bioactive | Concentration |
| Oroxylin A | 10-15% | Oroxylin A-7-glucuronide | 0.5-8% |
| Baicalein | 10-25% | Baicalein-7-glucuronide | 2-10% |
| Chrysin | 2-10% | Chrysin-7-glucuronide | 0.5-5% |

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

We claim:

1. A composition comprising 10%-15% w/w Oroxylin A, 10%-25% w/w Baicalein and 2%-10% w/w Chrysin, isolated from the bark of *Oroxylum indicum*.

2. The composition as in claim 1, wherein the said composition is obtained using a process comprising steps of:
   a) Cutting, drying and pulverising the bark of *Oroxylum indicum* into fine powder
   b) Extracting the fine powder of step a) with 80% methanol (v/v) to obtain an aqueous methanol extract
   c) Dissolving the aqueous methanol extract of step b) in water to yield a turbid solution
   d) Extracting the turbid solution of step c) using an organic solvent
   e) Concentrating and drying the solvent fraction of step d) to obtain a yellow brown colour powder
   f) Characterising bioactives present in the powder of step d) using HPLC, NMR and Mass spectrometry as Oroxylin A, as represented by STR #1, Baicalein, as represented by STR #2 and Chrysin, as represented by STR #3
   g) Standardising the isolated bioactives to contain not less than 10% of Oroxylin A, not less than 10% of Baicalein and not less than 2% of Chrysin

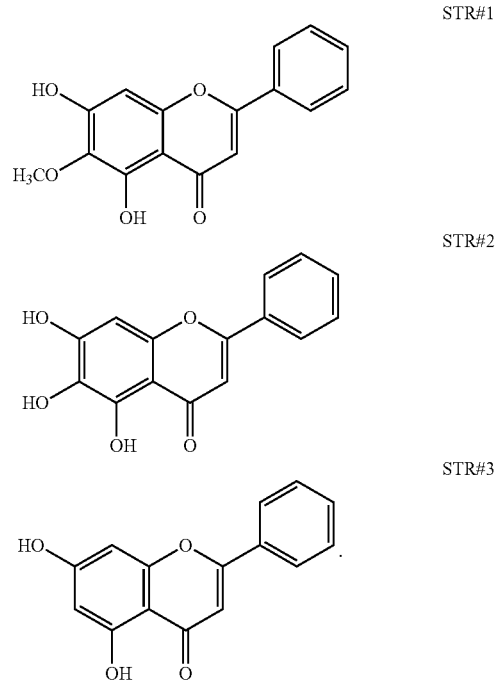

STR#1

STR#2

STR#3

* * * * *